United States Patent
Cajamarca et al.

(10) Patent No.: US 9,999,748 B2
(45) Date of Patent: Jun. 19, 2018

(54) FLEXIBLE CATHETER SHAFT AND METHOD OF MANUFACTURE

(71) Applicant: St. Jude Medical, Cardiology Division, Inc., St. Paul, MN (US)

(72) Inventors: Tobias Cajamarca, Plymouth, MN (US); Jeffrey John Strong, Coon Rapids, MN (US); Russell D. Terwey, St. Michael, MN (US); Bruce Robert Weir, Plymouth, MN (US); Janson Lee Ayer, Maple Grove, MN (US); Ryan Kenneth Buesseler, Delano, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 53 days.

(21) Appl. No.: 14/509,187

(22) Filed: Oct. 8, 2014

(65) Prior Publication Data
US 2015/0119862 A1  Apr. 30, 2015

Related U.S. Application Data

(60) Provisional application No. 61/895,171, filed on Oct. 24, 2013.

(51) Int. Cl.
*A61M 25/00* (2006.01)
*A61B 18/14* (2006.01)
(Continued)

(52) U.S. Cl.
CPC ..... *A61M 25/0051* (2013.01); *A61B 18/1492* (2013.01); *A61M 25/0013* (2013.01);
(Continued)

(58) Field of Classification Search
CPC ........ A61M 25/00045; A61M 25/0051; A61M 25/0013; A61M 25/0045; A61M 25/0052;
(Continued)

(56) References Cited

U.S. PATENT DOCUMENTS 3,650,277 A  3/1972  Sjostrand et al.
4,658,819 A  4/1987  Harris et al.
(Continued)

FOREIGN PATENT DOCUMENTS

EP  0667126  8/1995
WO  97/45157  12/1997
(Continued)

OTHER PUBLICATIONS

Dibona, Gerald F., Renal Innervation and Denervation: Lessons from Renal Transplantation Reconsidered, Artificial Organs, vol. 11, No. 6, 1987, 457-462.
(Continued)

*Primary Examiner* — Kami A Bosworth
*Assistant Examiner* — Tiffany Legette-Thompson
(74) *Attorney, Agent, or Firm* — Armstrong Teasdale LLP

(57) ABSTRACT

The present disclosure provides a strong, flexible catheter shaft for use in a catheter system. The flexible catheter shaft includes a nitinol tube having one or more sets of cuts therein in combination with one or more outer jacket layers. The flexible catheter shaft provides a shaft having sufficient stiffness and kink resistance to allow an operator to advance an electrode basket connected to the flexible catheter shaft through a guide catheter to a target ablation site without causing vessel trauma. The distal tip of the flexible catheter shaft is designed to have sufficient flexibility to reduce any risk of kicking out a guide catheter when tracking the electrode basket around turns in the vasculature of a patient.

17 Claims, 9 Drawing Sheets

(51) Int. Cl.
  *A61B 17/00* (2006.01)
  *A61B 18/00* (2006.01)
(52) U.S. Cl.
  CPC .............. *A61M 25/0045* (2013.01); *A61B 2017/00526* (2013.01); *A61B 2018/00267* (2013.01); *A61B 2018/1475* (2013.01); *Y10T 29/49812* (2015.01)
(58) Field of Classification Search
  CPC ...... A61M 25/0012; A61M 2205/0266; A61M 25/0138; A61M 25/0054; A61B 18/1492; A61B 2018/00267; A61B 2018/1475; A61B 2017/00526; A61B 1/71492; A61B 2018/00577; Y10T 29/49817; Y10T 29/49812
  USPC .................. 604/523, 524, 527, 528, 530
  See application file for complete search history.

(56) References Cited

U.S. PATENT DOCUMENTS

| | | | |
|---|---|---|---|
| 5,035,694 A | 7/1991 | Kasprzyk et al. | |
| 5,228,441 A | 7/1993 | Lundquist et al. | |
| 5,255,679 A | 10/1993 | Imran | |
| 5,300,068 A | 4/1994 | Rosar et al. | |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,893,885 A | 4/1999 | Webster, Jr. | |
| 5,897,553 A | 4/1999 | Mulier et al. | |
| 5,951,929 A * | 9/1999 | Wilson .............. | A61M 25/0009 264/138 |
| 5,954,649 A | 9/1999 | Chia et al. | |
| 5,954,719 A | 9/1999 | Chen et al. | |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Mulier et al. | |
| 6,117,101 A | 9/2000 | Diederich et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 2002/0068885 A1 | 6/2002 | Harhen et al. | |
| 2002/0120304 A1 | 8/2002 | Mest | |
| 2003/0050681 A1 | 3/2003 | Pianca et al. | |
| 2003/0060858 A1 | 3/2003 | Kieval et al. | |
| 2003/0069522 A1 * | 4/2003 | Jacobsen .......... | A61M 25/0013 600/585 |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2005/0288730 A1 | 12/2005 | Deem et al. | |
| 2006/0089678 A1 | 4/2006 | Shalev | |
| 2006/0264904 A1 * | 11/2006 | Kerby .............. | A61M 25/0014 604/523 |
| 2007/0083194 A1 * | 4/2007 | Kunis ................ | A61B 18/1815 606/41 |
| 2007/0135875 A1 | 6/2007 | Demarais et al. | |
| 2008/0125753 A1 * | 5/2008 | Chen ................ | A61M 25/0013 604/528 |
| 2008/0188928 A1 | 8/2008 | Salahieh et al. | |
| 2008/0255478 A1 | 10/2008 | Burdette | |
| 2009/0043283 A1 | 2/2009 | Turnlund et al. | |
| 2009/0076409 A1 | 3/2009 | Wu et al. | |
| 2009/0082723 A1 * | 3/2009 | Krogh .............. | A61B 1/00078 604/95.05 |
| 2010/0016762 A1 | 1/2010 | Thapliyal et al. | |
| 2010/0069882 A1 * | 3/2010 | Jennings .......... | A61M 25/0138 604/525 |
| 2010/0094209 A1 | 4/2010 | Drasler et al. | |
| 2010/0168737 A1 | 7/2010 | Grunewald | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0118726 A1 | 5/2011 | de la Rama et al. | |
| 2011/0137298 A1 | 6/2011 | Nguyen et al. | |
| 2011/0160720 A1 | 6/2011 | Johnson | |
| 2011/0213231 A1 | 9/2011 | Hall et al. | |
| 2011/0245808 A1 * | 10/2011 | Voeller ............ | A61M 25/0013 604/528 |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0172840 A1 * | 7/2012 | Guo .................. | A61L 29/085 604/523 |
| 2012/0296232 A1 | 11/2012 | Ng | |
| 2012/0323233 A1 | 12/2012 | Maguire et al. | |
| 2013/0046285 A1 | 2/2013 | Griffin et al. | |
| 2013/0116737 A1 | 5/2013 | Edwards et al. | |
| 2013/0131743 A1 | 5/2013 | Yamasaki et al. | |

(56) References Cited

U.S. PATENT DOCUMENTS

| | | | |
|---|---|---|---|
| 2013/0144251 | A1 | 6/2013 | Sobotka |
| 2013/0172715 | A1 | 7/2013 | Just et al. |

FOREIGN PATENT DOCUMENTS

| | | |
|---|---|---|
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2009085486 | 7/2009 |
| WO | 2012/064818 | 5/2012 |
| WO | 2012/106492 | 8/2012 |

OTHER PUBLICATIONS

Dibona, Gerald F., Role of the Renal Nerves in Renal Sodium Retention and Edema Formation, Trans Am Clin Climatol Assoc. 1990; 101: 38-45.

Dibona, Gerald F., Sympathetic Nervous System and Hypertension, Hypertension Journal of The American Heart Association, 2013; 61: 556-560.

Dibona, Gerald F., Sympathetic Nervous System and the Kidney in Hypertension, Curr Opin Nephrol Hypertens. Mar. 2002;11(2):197-200.

Dibona, Gerald F., The Sympathetic Nervous System and Hypertension, Hypertension Journal of The American Heart Association, Vo. 43, Feb. 2004, 147-150.

Doumas, Michael et al, Interventional Management of Resistant Hypertension, The Lancet, vol. 373, Apr. 11, 2009, pp. 1228-1230.

Dubuc, Marc et al, Feasibility of Cardiac Cryoablation Using a Transvenous Steerable Electrode Catheter, Journal of Interventional Cardiac Electrophysiology, 1998, 2: 285-292.

Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.

Esler, M. et al, Sympathetic Nerve Activity and Neurotransmitter Release in Humans: Translation from Pathophysiology into Clinical Practice, Scandinavian Physiological Society, 2003, 177, 275-284.

Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.

Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.

Evelyn, Kenneth A. et al, Effect of Thoracolumbar Sympathectomy on the Clinical Course of Primary (Essential) Hypertension, American Journal of Medicine, Feb. 1960, 188-221.

Freyberg, R. H. et al, The Effect on the Kidney of Bilateral Splanchnicectomy in Patients with Hypertension, The Journal of Clinical Investigation, vol. 16, Issue 1, Jan. 1937, 49-65.

Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.

Gazdar, A. F. et al, Neural Degeneration and Regeneration in Human Renal Transplants, The New England Journal of Medicine, vol. 238, No. 5, Jul. 1970, 222-224.

Goldberg, Michael R. et al, Reconstructive Vascular Surgery for Renovascular Hypertension, Can Med Assoc J. Feb. 2, 1974;110(3):275-80.

Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.

Gorisch, Wolfram et al, Heat-Induced Contraction of Blood Vessels, Lasers in Surgery and Medicine 2:1-13 (1982).

Grassi, Guido et al, Baroreflex Control of Sympathetic Nerve Activity in Essential and Secondary Hypertension, Hypertension Journal of The American Heart Association, 1998;31:68-72.

Grassi, Guido et al, Dissociation Between Muscle and Skin Sympathetic Nerve Activity in Essential Hypertension, Obesity, and Congestive Heart Failure, Hypertension. 1998;31:64-67.

Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.

Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.

Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.

Guyton, Arthur C., Blood Pressure Control Special Role of the Kidneys and Body Fluids, Science, vol. 252, Jun. 1991, 1813-1816.

Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

Hall, J.E. et al, Role of Sympathetic Nervous System and Neuropeptides in Obesity Hypertension, Brazilian Journal of Medical and Biological Research, 2000, 33:605-618.

Hall, John E., The Kidney, Hypertension, and Obesity, Hypertension. 2003;41:625-633.

Hall, Winthrop H. et al, Combined Embolization and Percutaneous Radiofrequency Ablation of a Solid Renal Tumor, American Journal of Roentgenology, 174, Jun. 2000, 1592-1594.

Hamm, Christian et al, Confluence, Issue eight, Apr. 2014.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6(4):270-6.

Howard, James P. et al, Size of Blood Pressure Reduction from Renal Denervation: Insights from Meta-Analysis of Antihypertensive Drug Trials of 4121 Patients with Focus on Trial Design: The CONVERGE Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1. 2014, pp. 29-35.

(56) References Cited

OTHER PUBLICATIONS

Howell, Marcus H. et al, Tandem Stenting of Crossed Renal Arteries with Ostial Stenosis, Tex Heart Inst J. 2000; 27(2):166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shoei K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of The American Heart Association, 1998;32:249-254.
Humpreys, Michael H., Renal Nerves and CKD: Is Renal Denervation the Answer?, Journal of The American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, JR, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.

(56) References Cited

OTHER PUBLICATIONS

Parmar, Arundhati, Analyst: Medtronic Will Likely Acquire Another Hypertension Therapy Firm, Medcity News, Apr. 27, 2012; 3:06 p.m.; medcitynews.com.

Pavlovich, Christian P. et al, Percutaneous Radio Requency Ablation of Small Renal Tumors: Initial Results; The Journal of Urology, vol. 167, Jan. 10-15, 2002.

Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.

Peet, Max Minor, Hypertension and Its Surgical Treatment by Bilateral Supradiaphragmatic Splanchnicectomy, American Journal of Surgery, vol. 75, Issue 1, Jan. 1948, 48-68.

Perry, C. Bruce, Malignant Hypertension Cured by Unilateral Nephrectomy, British Heart Journal, Jul. 1945; 7(3):139-142.

Persu, Alexandre et al, Renal Denervation: Ultima Ratio or Standard in Treatment-Resistant Hypertension, Hypertension Journal of The American Heart Association, Sep. 2012;60(3):596-606.

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.

Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.

Poutasse, Eugene F., Surgical Treatment of Renal Hypertension, American Journal of Surgery, vol. 107, Jan. 1964, 97-103.

Pugsley, M.K. et al, The Vascular System an Overview of Structure and Function, Journal of Pharmacological and Toxicological Methods 44 (2000) 333-340.

Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.

Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.

Rippy, Marian K. et al, Catheter-Based Renal Sympathetic Denervation: Chronic Preclinical Evidence for Renal Artery Safety, Clin Res Cardiol (2011) 100:1095-1101.

Ritz, Eberhard, New Approaches to Pathogenesis and Management of Hypertension, Clin J Am Soc Nephrol 4:1886-1891, 2009.

Zazgornik, Jan et al, Bilateral Nephrectomy: The Best, but Often Overlooked, Treatment for Refractory Hypertension in Hemodialysis Patients, AJH 1998; 11:1364-1370.

International Search Report and Written Opinion for Application PCT/US2014/059609 dated Dec. 15, 2014.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19/26, 2013:2029-30.

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the SYMPLICITY HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, GE et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labeit, Alexander Michael et al, Changes in the Prevalence, Treatment and Control of Hypertension in Germany? A Clinical-Epide-

(56) References Cited

OTHER PUBLICATIONS miological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After SYMPLICITY HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of The American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badder, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.

(56) References Cited

OTHER PUBLICATIONS

Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9:741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.

Dequattro V. et al, The Sympathetic Nervous System: The Muse of Primary Hypertension, Journal of Human Hypertension, 2002, 16 (Supp) 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, Eurolntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.

(56) References Cited

OTHER PUBLICATIONS

Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Von End, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.-Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and The United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.

* cited by examiner

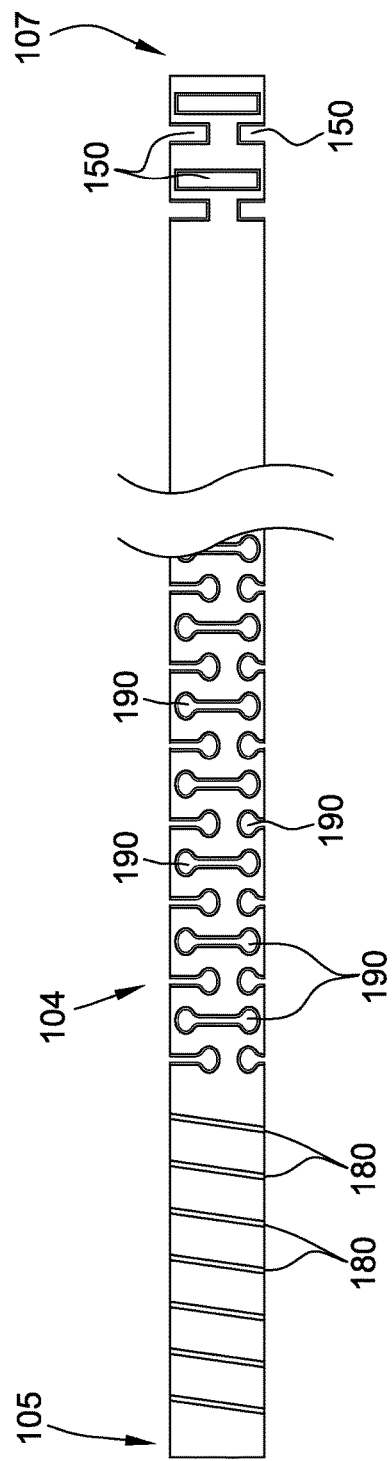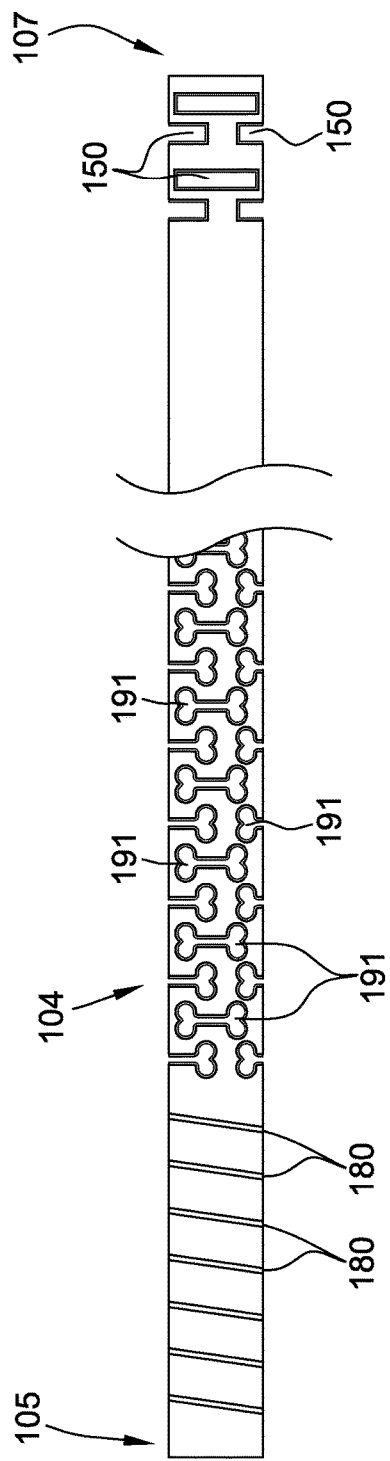

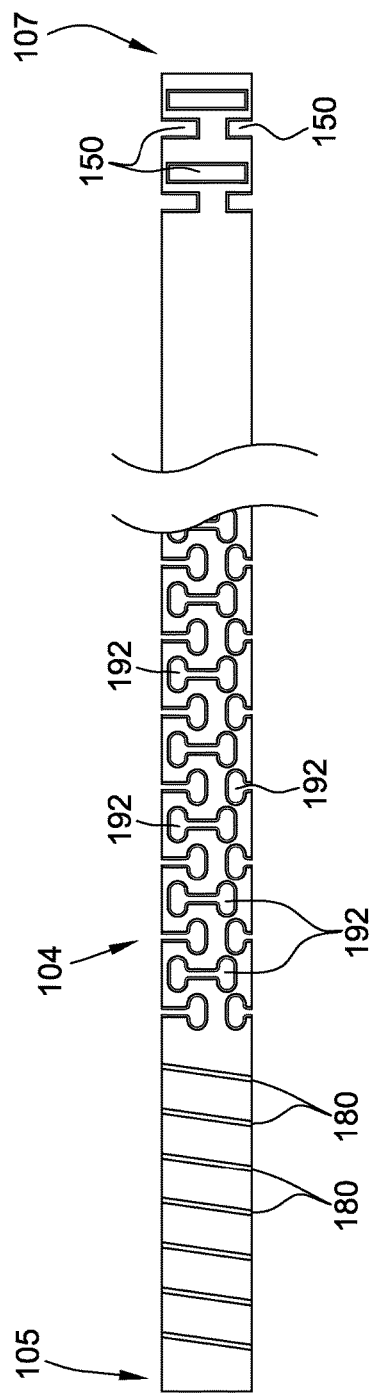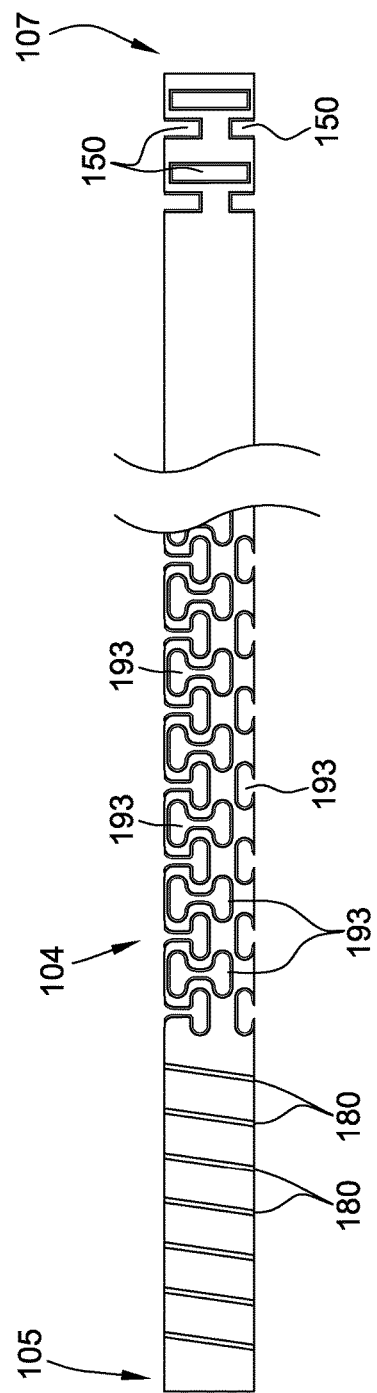

FLEXIBLE CATHETER SHAFT AND METHOD OF MANUFACTURE

CROSS-REFERENCE TO RELATED APPLICATIONS

This application claims priority to provisional application Ser. No. 61/895,171, filed Oct. 24, 2013, the entire specification of which is incorporated herein.

a. Field of the Disclosure

The present disclosure relates generally to catheters that are used in the human body. In particular, the present disclosure relates to a flexible catheter shaft including a nitinol tube having a series of cuts thereon to improve flexibility, kink resistance, column strength, and maneuverability of the catheter shaft.

b. Background Art

Catheter systems are well known in the art for use in medical procedures, such as diagnostic, therapeutic and ablative procedures. Typical catheter systems generally include an elongate flexible catheter shaft extending from a handle. A physician manipulates the catheter through the patient's vasculature to an intended site within the patient. The catheter typically carries one or more working components, such as electrodes and thermocouples, or other diagnostic, therapeutic or ablative devices for carrying out the procedures. One or more controls or actuators may be provided on the handle for selectively adjusting one or more characteristics of the working components.

Since the path through the patient's vasculature to the intended site is often long and tortuous, steering forces typically must be transmitted over relatively great distances. Accordingly, it is generally desirable for a catheter to have sufficient axial (e.g., column) strength to be pushed through the patient's vasculature via a force applied at its proximal end ("pushability"). It is also generally desirable for a catheter to transmit a torque applied at the proximal end to the distal end ("torqueability"). Pushability and torqueability (collectively, "maneuverability") permit an operator, such as a physician, to manipulate a catheter to an intended site and then properly orient the catheter during an ablation procedure. It is also generally desirable for a catheter, and specifically the catheter tip, to have sufficient flexibility to substantially conform to the patient's vasculature and yet resist kinking as it does so. Kinking is often the result of a localized failure of the material of the catheter when localized stresses exceed the yield strength of the material.

To provide the desired pushability, torqueability, flexibility, and kink resistance, many catheter shafts are made at least partially of thermoplastic polymer materials that may be reinforced with a secondary material. The desirable characteristics of pushability, torqueability, flexibility, and kink resistance are often in tension or conflict with one another, however, with improvements in one requiring compromises in another.

BRIEF SUMMARY OF THE DISCLOSURE

In one embodiment, the present disclosure is directed to a catheter shaft comprising a nitinol tube having a proximal end and a distal end, a spring coil disposed within the nitinol tube, and an outer jacket covering the nitinol tube. At least a portion of the distal end of the nitinol tube includes a set of cuts in the nitinol tube, and a pocket extends past the distal end of the nitinol tube.

In another embodiment, the present disclosure is directed to a catheter shaft comprising a nitinol tube having a proximal end and a distal end, a spring coil disposed within the nitinol tube, and an outer jacket covering the nitinol tube. At least a portion of the distal end of the nitinol tube includes at least two sets of cuts in the nitinol tube and at least a portion of the proximal end includes at least one set of cuts. A pocket extends past the distal end of the nitinol tube.

In another embodiment, the present disclosure is directed to a method of manufacturing a catheter shaft. The method comprises cutting a nitinol tube to form a first set of cuts and a second set of cuts different from the first set of cuts in a distal end of the nitinol tube; introducing a spring coil into the nitinol tube; introducing one or more polyether block amide tubes around the nitinol tube, wherein at least a portion of a polyether block amide tube extends past the distal end of the nitinol tube; introducing a mandrel inside of the spring coil; introducing a heat shrink material over the polyether block amide tubes; reflowing the polyether block amide tubes to form an outer jacket on the nitinol tube and a pocket extending past the distal end of nitinol tube; and removing the heat shrink material.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 7A-7D illustrate a nitinol tube including a spiral cutting pattern and various dog bone cutting patterns on a distal end.

Corresponding reference characters indicate corresponding parts throughout the several views of the drawings. It should be understood that the Figures as shown herein are not necessarily to scale.

DETAILED DESCRIPTION OF THE DISCLOSURE

The present disclosure provides a flexible catheter shaft suitable for use in the human vasculature for known medical procedures, such as renal ablation procedures. Catheters utilizing flexible catheter shafts according to the present disclosure advantageously exhibit improved maneuverability, flexibility, and kink resistance. For purposes of this description, the disclosure will be described in connection with an elongate electrophysiology catheter. It is contemplated, however, that the described features and methods may be incorporated into any number of catheters (e.g., steerable catheters, introducer catheters, and the like) as would be appreciated by one of ordinary skill in the art based on the disclosure herein.

More specifically, the present disclosure provides a strong, flexible catheter shaft that includes a nitinol tube having a series of cuts on at least a distal end. In many embodiments, the distal end will include two set of cuts on the distal end, with the two sets being of a different shape or pattern to improve flexibility and strength. The flexible catheter shaft further includes a spring coil and an outer jacket, which may be constructed of multiple materials having different characteristics. The flexible catheter shaft provides a shaft having sufficient stiffness and kink resistance to allow an operator to advance an electrode basket connected to the flexible catheter shaft through a guide catheter to a target ablation site without causing vessel trauma. The distal tip of the flexible catheter shaft is designed to have sufficient flexibility to reduce any risk of kicking out a guide catheter when tracking the electrode basket around various turns in the vasculature of a patient. In many embodiments, the flexible catheter shaft may be sized and configured to be used in combination with a 6 French guide catheter while still allowing sufficient room between the guide catheter and flexible catheter shaft for a contrast agent to pass. Although described in detail herein with regard to a 6 French guide catheter, one skilled in the art will recognize that the flexible catheter shaft may be sized and configured to be used with other size guide catheters and the like.

The flexible catheter shaft of the present disclosure additionally provides sufficient column strength to facilitate the opening of an electrode basket attached thereto through the use of an activation wire that is routed through the interior of the flexible catheter shaft, while maintaining a consistent length as it is tracked through a tortuous pathway inside of a patient. Additionally, the flexible catheter shaft provides controllable torque such that the electrode basket attached thereto can easily be rotated between ablation cycles, while maintaining a sufficiently large internal diameter to allow for the passage of the activation wire and other electrical wires to the handle of the catheter system. In one example, it can be rotated 45 degrees.

Figure 1:
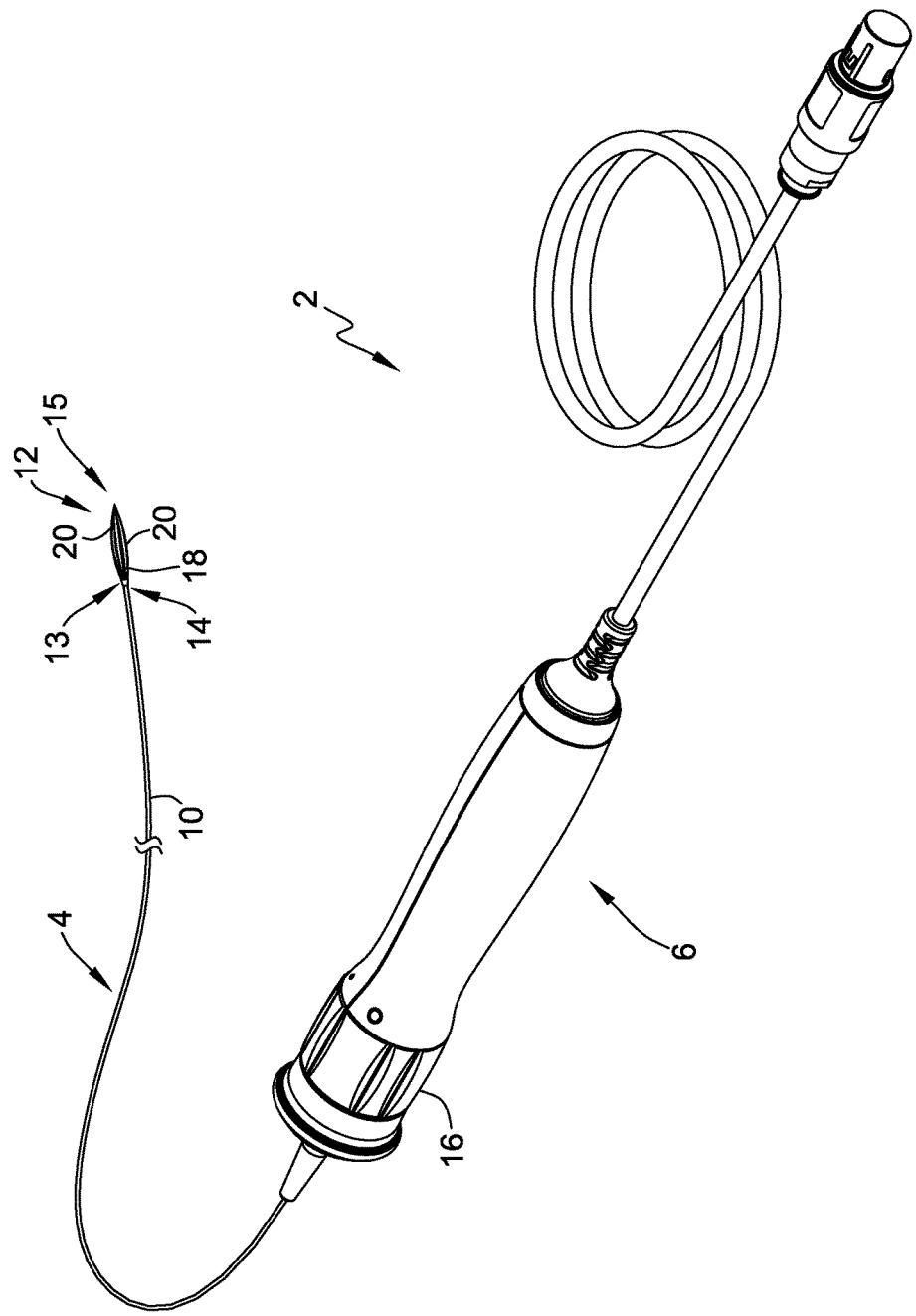
FIG. 1 is a perspective view of one embodiment of a catheter system including a handle, a catheter shaft, and an electrode assembly having multiple electrodes, with the electrode assembly being in a collapsed configuration.
Figure 2:
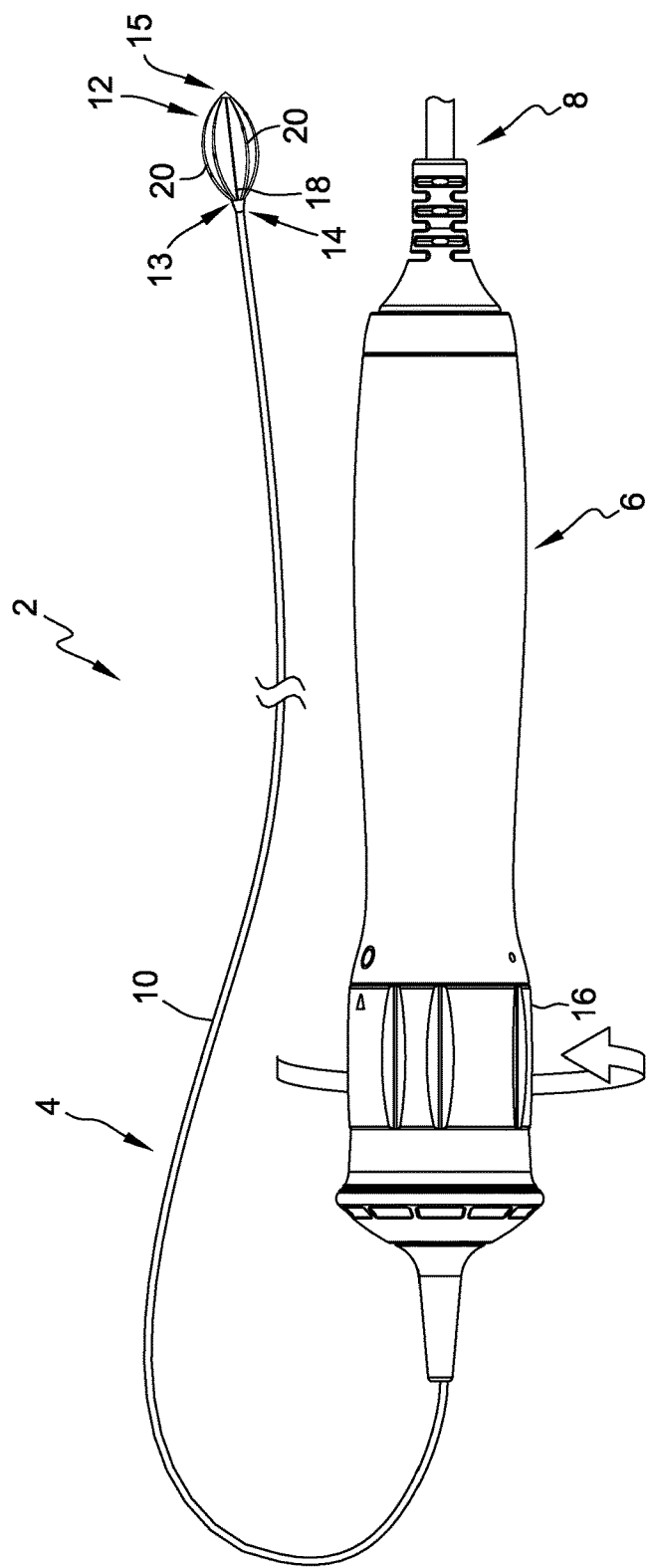
FIG. 2 is a side elevation of the catheter system of FIG. 1, with the electrode assembly being in an expanded configuration resulting from rotation of a rotatable actuator.

Referring now to the drawings, and in particular to FIGS. 1 and 2, a conventional catheter system 2 is shown by way of background and reference. Catheter system 2 includes a flexible catheter 4, a handle 6 to which flexible catheter 4 is connected, and a conductor assembly 8 for electrically connecting catheter system 2 to a suitable power supply (not shown). As one example, catheter system 2 illustrated and described herein is suitably constructed for use as an ablation system, such as a renal or heart ablation system. More particularly, illustrated catheter system 2 is a multi-electrode renal denervation system. One example of such a catheter system 2 is currently made by St. Jude Medical, Inc. under the trade name EnligHTN. General operation of a multi-electrode renal denervation system is known to those of skill in the art and is not described further herein except to the extent necessary to describe the present embodiments. It is also understood that catheter system 2 may be used for any other suitable treatment or purpose without departing from the scope of this disclosure. Additionally, while catheter system 2 is illustrated and described herein as including flexible catheter 4, catheter system 2 may further include other components used, for example, to guide flexible catheter 4 into the patient—such as, without limitation, a relatively more rigid guide catheter (not shown) or guide wire (not shown).

Flexible catheter 4 includes an elongate, flexible hollow shaft 10 connected to handle 6 at or near a proximal or rear end of the catheter shaft (not shown because it is hidden by a connector at the front end of handle 6), and an electrode assembly 12 disposed at or near a distal or front end 14 of flexible hollow shaft 10. Electrode assembly 12 includes proximal end 13 and distal end 15. It is understood, however, that electrode assembly 12 may be disposed anywhere along flexible hollow catheter shaft 10 intermediate the proximal end and the distal end 14 thereof without departing from the scope of this disclosure. As used herein, the terms proximal and front, and distal and rear, are used with reference to the orientation of catheter system 2 illustrated in the various drawings and for the purpose of describing the various embodiments set forth herein, and are not intended as limiting the catheter system and related components to having any particular orientation upon assembly or during operation thereof. In particular, the terms proximal and rear refer to a longitudinal position that is relatively nearer to handle 6 while the terms distal and front refer to a longitudinal position that is relatively farther from handle 6.

Illustrated electrode assembly 12 is in the form of what may be referred to as an electrode basket and includes struts 20, and is suitably configurable between a collapsed configuration (FIG. 1) for maneuvering and positioning the electrode assembly in the patient, and an expanded configuration (FIG. 2) for operation of the electrode assembly to perform a desired procedure such as an ablation procedure. An annular (e.g., ring-shaped) actuator 16 is mounted on handle 6 for rotation relative thereto and is operatively connected to electrode assembly 12 for selectively configuring the electrode assembly between its collapsed and expanded configurations. It is understood that another suitable actuator (e.g., slide, push button, lever, etc.) may be used instead of rotating actuator 16 to selectively configure electrode assembly 12 without departing from the scope of this disclosure. In some embodiments, electrode assembly 12 may be selectively adjustable between an infinite number of configurations (e.g., degrees of expansion) between its collapsed and expanded configurations using actuator 16.

A control line, such as a suitable cable or pull wire 18 extends from electrode assembly 12 within hollow catheter shaft 10 and into the handle 6 for operative connection with the actuator to thereby operatively connect the actuator 16 with electrode assembly 12. In some embodiments two or more pull wires, cables or other suitable control lines or tubes may be used for selectively configuring electrode assembly 12. It is also understood that control line 18 may be any suitable control line other than a pull wire, such as a cable, string, tie, compression member or other suitable control to operatively connect electrode assembly 12 to actuator 16. A suitable electrical wire bundle (not shown) also extends through hollow catheter shaft 10 from handle 6 to electrode assembly 12 to deliver power to, and receive feedback from, electrode assembly 12.

As noted herein, the flexible catheter shaft of the present disclosure includes a nitinol tube having a distal end and a proximal end, a spring coil disposed inside of the nitinol tube, an outer jacket covering the nitinol tube, and a pocket that extends past the distal end of the nitinol tube. The flexible catheter shaft is sized and configured to be attached at the distal end to a suitable electrode basket (i.e., the electrode basket fits inside of the pocket) and attached at the proximal end to a catheter handle. The nitinol tube includes at least one set of cuts on at least a portion of the distal end, and in many desirable embodiments, includes at least a first set of cuts and a second set of cuts on the distal end, wherein the first set of cuts is different from the second set of cuts. Further, in many embodiments, the proximal end of the nitinol tube will also include a first set of cuts. The cuts in the nitinol tube on the distal end are introduced thereon to facilitate flexibility of the distal end and tip upon use of the flexible catheter shaft, as well as to facilitate the locking of the spring coil to the distal end of the nitinol tube during manufacturing as disclosed herein. The cuts in the nitinol tube on the proximal end are introduced thereon to facilitate the locking of the spring coil to the proximal end of the nitinol tube during manufacturing, also as disclosed herein.

Figure 3:
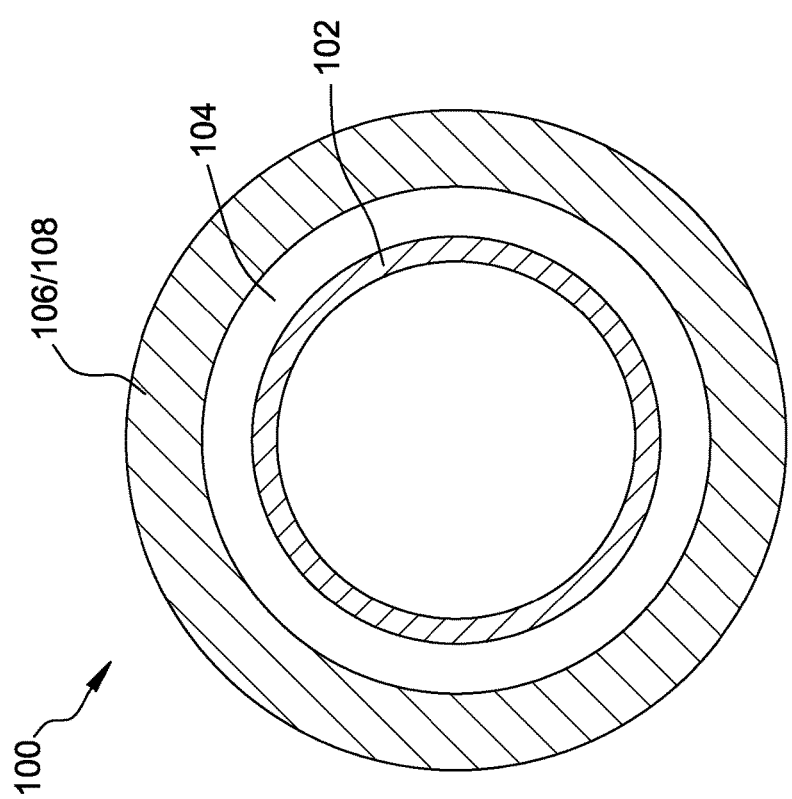
FIG. 3 is an axial cross-sectional view showing various components of a flexible catheter shaft in accordance with the present disclosure.
Figure 4:
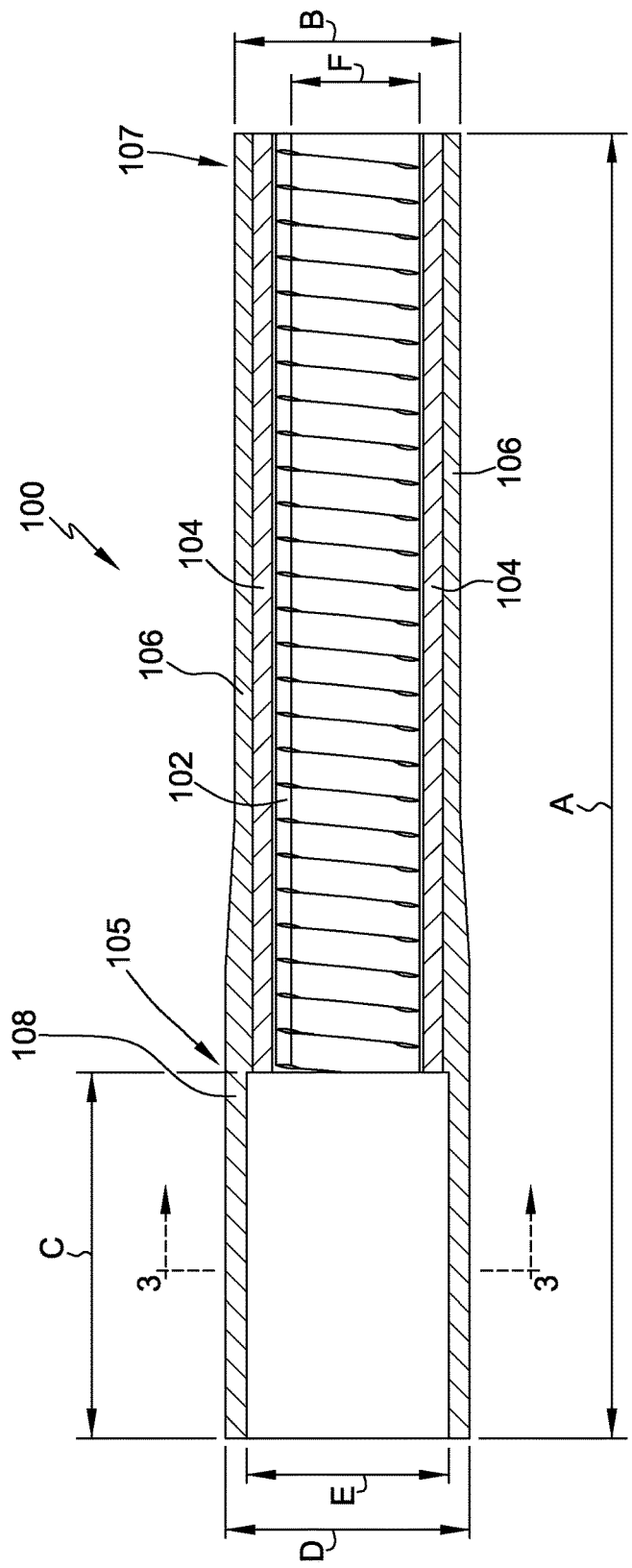
FIG. 4 is a longitudinal cross-sectional view showing various components of a flexible catheter shaft in accordance with the present disclosure.

Referring now to FIGS. 3 and 4, there is shown a flexible catheter shaft 100 in accordance with the present disclosure that includes nitinol tube 104 having distal end 105 and proximal end 107. Nitinol tube 104 has spring coil 102 disposed therein. Outer jacket 106 covers nitinol tube 104, and pocket 108 extends past distal end 105 of nitinol tube 104. As noted above, nitinol tube 104 includes various cuts on distal end 105 (not shown in FIGS. 3 and 4) and optionally proximal end 107 (not shown in FIGS. 3 and 4).

Referring now to FIG. 4, which as noted above is not necessarily drawn to scale, flexible catheter shaft 100, including pocket 108, has a length A an outer diameter B and an inner diameter F at proximal end 107 of flexible catheter shaft 100. Pocket 108 has a length C extending from distal end 105 of flexible catheter shaft 100 and has an outer diameter D and an inner diameter E. In many embodiments of the present disclosure, flexible catheter shaft 100 is sized and configured to allow for easy insertion through a 6 French guide catheter and to allow a contrast agent to be passed between flexible catheter shaft 100 and guide catheter during a procedure. Although generally sized and configured for insertion through a 6 French guide catheter, flexible catheter shaft 100 may be sized and configured for insertion through other sized guide catheters in accordance with the present disclosure.

In many embodiments, length A will be from about 20 inches (about 50.8 centimeters) to about 80 inches (about 203.2 centimeters), including from about 30 inches (about 76.2 centimeters) to about 60 inches (about 152.4 centimeters), including from about 40 inches (about 101.6 centimeters) to about 60 inches (about 152.4 centimeters). In some embodiments, length A may be about 41 inches (about 104.1 centimeters), or about 42 inches (about 106.7 centimeters), or about 43 inches (about 109.2 centimeters) or about 44 inches (about 111.8 centimeters) or even about 45 inches (about 114.3 centimeters). In other embodiments, length A may be about 60 inches (about 152.4 centimeters) or even about 61 inches (about 154.9 centimeters). Outer diameter B may generally be less than 0.0650 inches (0.1651 centimeters), or even less than 0.0630 inches (0.1600 centimeters), or even less than 0.0610 inches (0.1549 centimeters). In some embodiments, outer diameter B may be about 0.0600 inches (about 0.1524 centimeters). Length C may generally be at least 0.075 inches (0.1905 centimeters), or at least 0.090 inches (0.229 centimeters), or even at least 0.150 inches (0.381 centimeters). In many embodiments, length C will be about 0.160 inches (about 0.406 centimeters). Outer diameter D may generally be less than 0.067 inches (0.170 centimeters), or even less than 0.066 inches (0.168 centimeters). In many embodiments, outer diameter D may be about 0.065 inches (about 0.165 centimeters). Inner diameter E may generally be less than 0.060 inches (0.152 centimeters), or even less than 0.058 inches (0.147 centimeters). In some embodiments, inner diameter E may be about 0.056 inches (about 0.142 centimeters. Inner diameter F may generally be less than 0.055 inches (0.139 centimeters), or even less than 0.052 inches (0.132 centimeters). In many embodiments, inner diameter F may be about 0.050 inches (about 0.127 centimeters). Of course, one skilled in art will recognize based on the disclosure herein that one or more of these dimensions may be changed depending upon exact design specifications.

Nitinol tube 104 comprises a unitary tube of nitinol having superior superelastic properties. While other materials having superelastic properties similar to nitinol are within the scope of the present disclosure, nitinol is generally desirable. Nitinol is an approximately stoichiometric alloy of nickel and titanium, which may also include minor amounts of other metals to achieve desired properties. Nickel-titanium alloys are very elastic and are commonly referred to as "superelastic" or "pseudoelastic." In many embodiments, the nitinol tube will have an outer diameter of from about 0.0400 inches (about 0.1016 centimeters) to about 0.0500 inches (about 0.127 centimeters), including about 0.0480 inches (about 0.1219 centimeters), and an inner diameter of from about 0.0400 inches (about 0.101 centimeters) to about 0.0500 inches (about 0.127 centimeters), including about 0.0420 inches (0.107 centimeters). In addition, in many embodiments, the nitinol tube will have a wall thickness of from about 0.003 inches (about 0.00762 centimeters) to about 0.006 inches (about 0.01524 centimeters), including from about 0.003 inches (about 0.00762 centimeters) to about 0.005 inches (about 0.0127 centimeters).

As noted above, the nitinol tube component of the flexible catheter shaft generally includes various cuts and patterns therein to facilitate both improved flexibility of the catheter shaft, and also assist in locking in place the spring coil disposed within the nitinol tube. Generally, the nitinol tube will include at least one set of cuts on the distal end of the nitinol tube to increase the flexibility of the flexible catheter shaft and assist in locking down the spring coil disposed within the nitinol tube as noted herein. In many embodiments, the nitinol tube will include at least two sets of cuts on the distal end of the nitinol tube, where the first set of cuts will be of a different shape than the second set of cuts. Additionally, in other embodiments where the distal end of the nitinol tube may include a single set of cuts or two or more sets of cuts, the proximal end may also include a set of cuts to facilitate the locking down of the spring coil disposed within the nitinol tube at the proximal end. The cuts on the proximal end may be of the same or different shape as the first and/or second set of cuts.

The cuts and cut patterns introduced onto the nitinol tube, either at the distal end only or at both the distal end and the proximal end, may be of any cut style or pattern sufficient to improve the flexibility of the nitinol tube and/or facilitate in the locking down of the inner spring coil. For example, the cuts may be in the form of spiral cuts, window cuts, dog bone cuts (see FIGS. 7 and 7A-7C, discussed in detail below), combinations of these, any other suitable cut pattern. In many embodiments, the distal end of the nitinol tube will include a first set of cuts and a second set of cuts, with the first set of cuts being of a different pattern than the first set of cuts.

Figure 5:
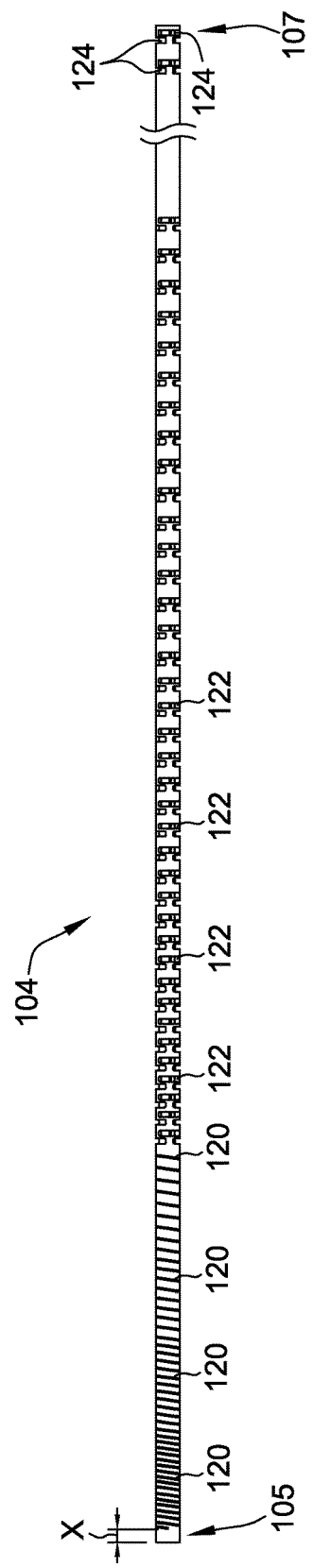
FIG. 5 illustrates a nitinol tube including various cutting patterns on the surface thereof.

Referring now to FIG. 5, there is shown nitinol tube 104 having distal end 105 and proximal end 107. Nitinol tube 104 additionally includes a first set of cuts 120 and a second set of cuts 122 on distal end 105 and a third set of cuts 124 on proximal end 107. First set of cuts 120 on distal end 105 is different than second set of cuts 122 on distal end 105. First set of cuts 120 are illustrated in FIG. 5 in a spiral formation, while second set of cuts 122 are illustrated in a window formation. By including two different cut patterns on distal end 105 of nitinol tube 104, the flexibility of nitinol tube 104, and hence the flexible catheter shaft incorporating nitinol tube 104, can be controlled and customized.

In many embodiments, the first set of cuts (illustrated in FIG. 5 as first set of cuts 120) will extend on nitinol tube 104 (towards proximal end 107) for a distance of about 0.25 inches (about 0.635 centimeters), or even about 0.50 inches (about 1.27 centimeters), or even about 0.75 inches (about 1.91 centimeters), or even about 0.90 inches (about 2.29 centimeters), or even about 1 inch (about 2.54 centimeters) or more. In some embodiments, first set of cuts 120 will begin at the end of distal end 105, and in other embodiments, first set of cuts 102 will begin at a distance X from the end of distal end 105, as illustrated in FIG. 5. Distance X may be, for example, 0.010 inches (0.025 centimeters), or even 0.020 inches (0.051 centimeters), or even 0.030 inches (0.076 centimeters), or even 0.040 inches (0.102 centimeters). In one embodiment, distance X may be about 0.034 inches (about 0.086 centimeters).

Second set of cuts 122 may extend on nitinol tube 104 (towards proximal end 107) for a distance of about 1 inch (about 2.54 centimeters), or even 2 inches (5.08 centimeters), or even 3 inches (7.62 centimeters), or even 4 inches (10.16 centimeters), or even 5 inches (12.7 centimeters), or even 6 inches (15.24 centimeters) or more. In one embodiment, second set of cuts 122 extends on nitinol tube 104 for a distance of about 5 inches (about 12.7 centimeters). As such, in many embodiments, the total distance that first set of cuts 120 and second set of cuts 122 extend on nitinol tube 104 is about 5 inches (about 12.7 centimeters), or even about 6 inches (15.24 centimeters), or even about 7 inches (about 17.78 centimeters). In one desirable embodiment, the total distance that first set of cuts 120 and second set of cuts 122 extend on nitinol tube 104 is about 6 inches (about 15.24 centimeters).

Third set of cuts 124 on proximal end 107 may extend from proximal end 107 (toward distal end 105) for a distance of about 0.1 inches (about 0.254 centimeters), or even 0.25 inches (0.635 centimeters), or even 0.5 inches (1.27 centimeters), or even 1 inch (2.54 centimeters). In a desirable embodiment, third set of cuts 124 on proximal end extends about 0.5 inches (about 1.27 centimeters). As noted, third set of cuts 124 is primarily used to assist in locking down the spring coil at the proximal end.

Figure 6:
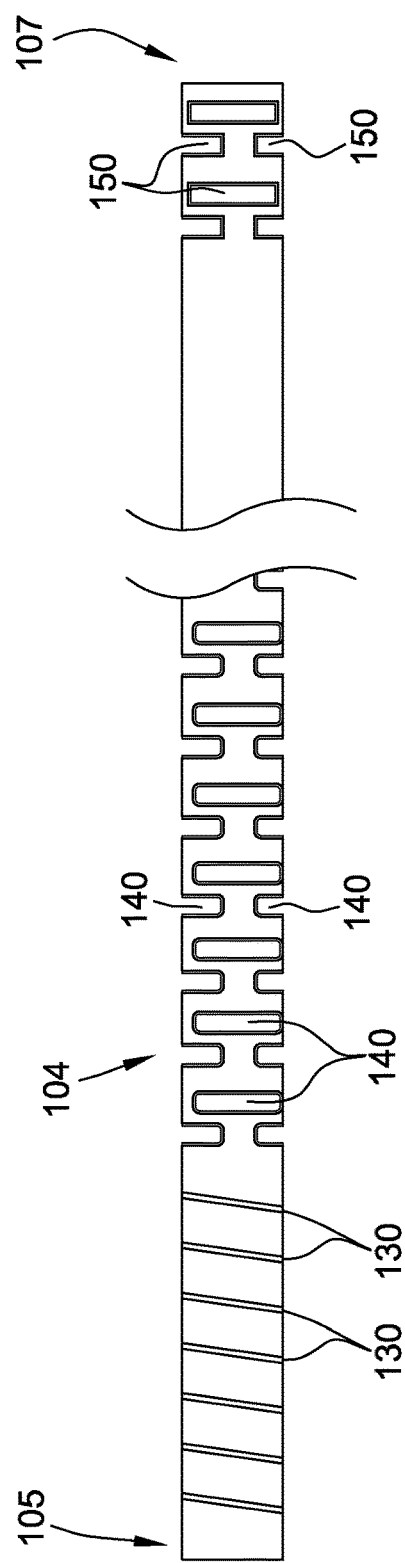
FIG. 6 illustrates a nitinol tube including a spiral cutting pattern and a window cutting pattern on a distal end.

Referring now to FIG. 6, there is shown one specific embodiment of a nitinol tube as disclosed in the present disclosure. FIG. 6 shows nitinol tube 104 having distal end 105 and proximal end 107. Distal end 105 includes first set of cuts 130 and second set of cuts 140. First set of cuts 130 are in a spiral pattern and second set of cuts 140 are in a window pattern. Proximal end 107 includes a third set of cuts 150 that are also in a window pattern. First set of cuts 130 and second set of cuts 140 impart flexibility to nitinol tube 104, and first set of cuts 130 and second set of cuts 150 also assist in locking down a spring coil (not shown) that is disposed inside of nitinol tube 104 during a reflowing process during manufacturing as described below in more detail.

Referring now to FIGS. 7A-7D, there is shown another specific embodiment of a nitinol tube as disclosed in the present disclosure. FIGS. 7A-7D show nitinol tube 104 having distal end 105 and proximal end 107. Distal end 105 includes first set of cuts 180 and second set of cuts 190, 191, 192, and 193. First set of cuts 180 are in a spiral pattern and second set of cuts 190 (FIG. 7A), 191 (FIG. 7B), 192 (FIG. 7C), and 193 (FIG. 7D) are in a dog bone pattern. Proximal end 107 includes a third set of cuts 195 that are in a window pattern. First set of cuts 180 and second set of cuts 190, 191, 192, and 193 impart flexibility to nitinol tube 104 by reducing strain on nitinol tube 104. First set of cuts 180 and second set of cuts 190, 191, 192, and 193 also assist in locking down a spring coil (not shown) that is disposed inside of nitinol tube 104 during a reflowing process during manufacturing as described below in more detail. The dog bone pattern as illustrated in FIGS. 7A-7D allows for the flexibility of nitinol tube 104 to be customized as desired. In particular, in one embodiment, the spacing or placement of second set of cuts 190 would be sufficiently small such that during flexing of nitinol tube 104, second set of cuts 190 contact one another, thereby limiting motion and providing another degree of freedom for the design and performance of nitinol tube 104. Further, by modifying the dog bone pattern, such as is shown in FIGS. 7B-7D, the strain imposed on nitinol tube 104 at various points may be better distributed across nitinol tube 104. In particular, for example, the strain could be distributed across the larger end portions of the dog bone shape shown in FIGS. 7B and 7C, or could be distributed within the area between the cuts as shown in FIG. 7D.

As noted above, the flexible catheter shaft described herein includes a spring coil disposed within the nitinol tube described above to impart further flexibility and strength to the nitinol tube, and hence the flexible catheter shaft including these components. Although the spring coil may be disposed within only a portion or portions of the nitinol tube (i.e., less than the entire length of the nitinol tube), it is generally desirable for the spring coil to be disposed within the nitinol tube such that it runs the entire length of the nitinol tube; that is, it is generally desirable that the nitinol tube and the spring coil be the same or similar length. Suitable spring coils (also commonly referred to in the art as rigidity compression coils) are well known in the art and commercially available from, for example, Motion Dynamics (Fruitport Charter Township, Mich.). One suitable example of a spring coil for use in the present disclosure has an outer diameter of about 0.040 inches (about 0.102 centimeters), an inner diameter of about 0.030 inches (about 0.076 centimeters), and is a rolled flat wire (about 0.0050 inches by about 0.0150 inches) (about 0.013 centimeters by about 0.038 centimeters). Based on the disclosure herein, one skilled in art will recognize that many other commercially available spring coils may be suitable for use in the present disclosure.

As mentioned above, the flexible catheter shaft additionally includes an outer jacket that covers the nitinol tube and additionally forms the pocket that extends from the distal end of the nitinol tube, and is sized and configured for receiving at least a proximal end of an electrode basket. The outer jacket (and the pocket) may be comprised of a single material, or may be comprised of multiple materials having differing strengths and stiffnesses; that is, the outer jacket that covers one portion of the length of the flexible catheter shaft (and pocket) may be constructed of a different material than the outer jacket that covers a different portion of the length of the flexible catheter shaft (and pocket). In many embodiments, the outer jacket and pocket are comprised of two, three or more different materials as described herein to depart desired characteristics to the flexible catheter shaft.

Suitable materials for constructing the outer jacket and pocket as described herein include, for example, thermoplastics, polystyrene, polyvinyl chloride, ethylene vinyl acetate, polyurethanes (urethane-based materials), nylon, polyether block amides (Pebax®), and the like. Other heat settable plastics or superplastics are also suitable and known to those of ordinary skill in the art. Particularly desirable thermoplastic materials include Pebax® polyether block amides. In many embodiments, two or three different Pebax® materials, each with a different durometer value, are used to construct the outer jacket and pocket.

Figure 8:
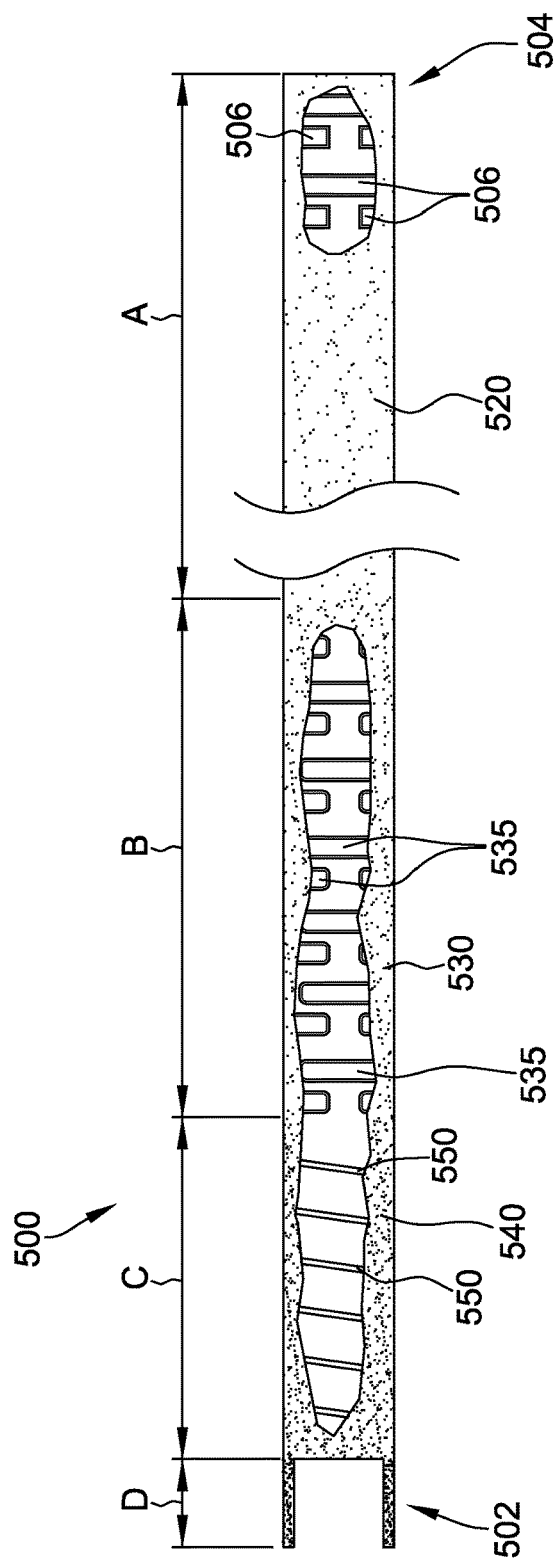
FIG. 8 illustrates a flexible catheter shaft of the present disclosure with sections cut away to reveal internal construction and having multiple outer jackets.

In one specific example, the outer jacket covering the nitinol tube (and forming the pocket) comprises three different Pebax® materials, each with a different durometer value to customize the flexibility and stiffness at various locations on the flexible catheter shaft. Referring now to FIG. 8, which illustrates a flexible catheter shaft of the present disclosure with sections cut away to reveal internal construction, there is shown flexible catheter shaft 500 including pocket 502 and proximal end 504. FIG. 8 also illustrates various sections of flexible catheter shaft 500 that each include an outer jacket comprised of a material having a different durometer value.

Specifically, FIG. 8 shows Zone A having outer jacket 520 and including proximal end 504 of flexible catheter shaft 500 including a third set of window cuts 506. Zone A may, for example, have a length of about 36.5 inches (about 92.71 centimeters). FIG. 8 also shows Zone B having outer jacket 530 and including the length of flexible catheter shaft 500 having a second set of window cuts 535. Zone B may, for example, have a length of about 5 inches (about 12.7 centimeters). Also shown in FIG. 8 is Zone C having an outer jacket 540 and including the length of flexible catheter shaft 500 having a first set of spiral cuts 550. Zone C may, for example, have a length of about 1 inch (about 2.54 centimeters). Also shown in FIG. 8 is pocket 502 that may, for example, have a length of about 0.160 inches (about 0.406 centimeters).

In the embodiment illustrated in FIG. 8, outer jacket 520 (Zone A) may be constructed from a Pebax® material having a durometer value of about 72, outer jacket 530 (Zone B) may be constructed from a Pebax® material having a durometer value of about 55, and outer jacket 540 (Zone C) may be constructed from a Pebax® material having a durometer value of about 35. Pocket 502 (Zone D) may be constructed from a Pebax® material having a durometer value of about 72. As such, in this illustrated embodiment, three different Pebax® materials, each having a different durometer value, are used to construct flexible catheter shaft 500. Of course, one skilled in the art based on the disclosure herein will recognize that many combinations of durometer values could be used to construct the various outer jacket sections within the scope of the present disclosure.

The flexible catheter shaft of the present disclosure may be manufactured by any suitable methodology based on the disclosure herein. In one example of a suitable manufacturing process, an appropriately sized nitinol tube is selected and the desired cuts introduced onto the surface thereof. The desired cuts, which may include a first (on a distal end), second (on a distal end), and third (on a proximal end) set of cuts as described herein, may be introduced to any suitable cutting method including, for example, laser cutting, sawing, chemical etching, and the like. Once the desired cuts have been introduced onto the nitinol surface at the appropriate locations, a suitable spring coil is introduced inside of the nitinol tube.

After the spring coil has been positioned inside of the nitinol tube, the material to be used for the outer jacket, such as a Pebax® or related material, is introduced around the exterior of the nitinol tube. The outer jacket material will generally be in the form of a tube that is slipped over the nitinol tube for further processing and reflowing. Of course, if the outer jacket as described herein is to be constructed of more than one material (that is, from materials having different durometer values), different tubes may be slipped over the desired area of the nitinol tube to form the final outer jacket. Once the desired tube or tubes of material for forming the outer jacket have been introduced over the nitinol tube and positioned, a mandrel is introduced inside of the spring coil. The mandrel is used to assist in forming the pocket as described herein, as well as to keep the outer jacket material from flowing into the interior of the spring coil.

Once the mandrel has been positioned, heat shrink material is introduced over the tube or tubes used to form the outer jacket and pocket, and the entire assembly introduced into a reflow oven and the outer jacket material reflowed to form the outer jacket and pocket over the mandrel. During the reflow process, reflowed outer jacket material will flow through cuts in the nitinol tube material at the distal and proximal end and lock in place the spring coil. After the reflow is complete and has been allowed to cool, the heat shrink material and mandrel are removed to produce a final flexible catheter shaft. In some embodiments where two or more tubes of material, such as tubes of Pebax®, are used to form the outer jacket and pocket, it may be desirable to apply axial pressure to the nitinol tube during the reflow process to further the joining of the various tubes of material into a single, substantially continuous outer jacket.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter shaft comprising a nitinol tube having a proximal end and a distal end, a spring coil disposed within the nitinol tube, and an outer jacket covering the nitinol tube and substantially continuous along an outer surface from a proximal end of the outer jacket to a distal end of the outer jacket, wherein at least a portion of a distal section of the nitinol tube includes a set of cuts in the nitinol tube, wherein the outer jacket includes a pocket formed therefrom and extending distally past the distal end of the nitinol tube, a maximum diameter of the pocket being larger than a diameter of the outer jacket at a proximal end thereof, wherein the pocket is configured for receiving at least a portion of an electrode basket therein, and wherein the outer jacket extends radially through at least one cut of the set of cuts to the spring coil.

2. The catheter shaft of claim 1 wherein a proximal section of the nitinol tube includes a first set of cuts.

3. The catheter shaft of claim 1 wherein the outer jacket comprises at least two separate polyether block amides.

4. The catheter shaft of claim 1 wherein the outer jacket comprises a material selected from the group consisting of a polyether block amide, a thermoplastic, a nylon, and combinations thereof.

5. The catheter shaft of claim 1 wherein the spring coil is a flat wound coil.

6. The catheter shaft of claim 1 wherein the pocket comprises a polyether block amide.

7. The catheter shaft of claim 1 wherein the catheter shaft has an outer diameter at the distal end of less than 0.067 inches.

8. The catheter shaft of claim 1 wherein the distal section of the nitinol tube includes a first set of cuts and a second set of cuts different than the first set of cuts.

9. The catheter shaft of claim 8 wherein the first set of cuts are in the form of spiral cuts and the second set of cuts are in the form of window cuts.

10. The catheter shaft of claim 8 wherein the first set of cuts are in the form of spiral cuts and the second set of cuts are in the form of dog bone cuts.

11. The catheter shaft of claim 1 wherein the outer jacket comprises a polyether block amide.

12. The catheter shaft of claim 11 wherein the outer jacket comprises at least three separate polyether block amides.

13. A catheter shaft comprising a nitinol tube having a proximal end and a distal end, a spring coil disposed within the nitinol tube, and an outer jacket covering the nitinol tube and substantially continuous along an outer surface from a proximal end of the outer jacket to a distal end of the outer jacket, wherein at least a portion of a distal section of the nitinol tube includes at least two sets of cuts in the nitinol tube and at least a portion of a proximal section includes at least one set of cuts, wherein the outer jacket includes a pocket formed therefrom and extending distally past the distal end of the nitinol tube, a maximum diameter of the pocket being larger than a diameter of the outer jacket at a proximal end thereof, wherein the pocket is configured for receiving at least a portion of an electrode basket therein, and wherein the outer jacket extends radially to the spring coil through at least one of: (i) at least one cut of the at least two sets of cuts on the distal section of the nitinol tube, and (ii) at least one cut of the at least one set of cuts on the proximal section of the nitinol tube.

14. The catheter shaft of claim 13 wherein the outer jacket is reflowed onto the nitinol tube such that the outer jacket secures the spring coil to the nitinol tube at the proximal end and the distal end of the nitinol tube.

15. The catheter shaft of claim 13 wherein the at least two sets of cuts on the distal section of the nitinol tube include a first set of spiral cuts and a second set of window cuts.

16. The catheter shaft of claim 13 wherein the at least two sets of cuts on the distal end of the nitinol tube include a first set of spiral cuts and a second set of dog bone cuts.

17. The catheter shaft of claim 13 wherein a portion of the outer jacket covering the proximal section of the nitinol tube comprises a polyether block amide having a durometer of about 55, a portion of the outer jacket covering the distal section of the nitinol tube comprises a polyether block amide having a durometer of about 35, and wherein the pocket is comprised of a polyether block amide having a durometer of about 72.

* * * * *